United States Patent
Palo et al.

(10) Patent No.: US 9,776,935 B2
(45) Date of Patent: Oct. 3, 2017

(54) METHOD FOR OLEFINS PRODUCTION

(75) Inventors: Emma Palo, Rome (IT); Gaetano Iaquaniello, Rome (IT)

(73) Assignee: STAMICARBON B.V. ACTING UNDER THE NAME OF MT INNOVATION CENTER, Sittard (NL)

( * ) Notice: Subject to any disclaimer, the term of this patent is extended or adjusted under 35 U.S.C. 154(b) by 304 days.

(21) Appl. No.: 14/005,542

(22) PCT Filed: Mar. 28, 2012

(86) PCT No.: PCT/NL2012/050201
§ 371 (c)(1),
(2), (4) Date: Sep. 16, 2013

(87) PCT Pub. No.: WO2012/134284
PCT Pub. Date: Oct. 4, 2012

(65) Prior Publication Data
US 2014/0018594 A1      Jan. 16, 2014

(30) Foreign Application Priority Data

Mar. 29, 2011   (EP) .................................... 11160218

(51) Int. Cl.
*C07C 5/32*     (2006.01)
*B01D 53/22*   (2006.01)
*C07C 5/333*   (2006.01)

(52) U.S. Cl.
CPC .............. *C07C 5/321* (2013.01); *B01D 53/22* (2013.01); *C07C 5/3335* (2013.01);
(Continued)

(58) Field of Classification Search
CPC ..... C07C 5/3335; C07C 11/02; C07C 5/3337; C07C 5/321; B01D 53/22
See application file for complete search history.

(56) References Cited

U.S. PATENT DOCUMENTS 3,904,703 A        9/1975  Lo et al.
4,313,013 A *     1/1982  Harris ..................... C07C 7/144
                                                            585/440
(Continued)

FOREIGN PATENT DOCUMENTS

GB        1039381        8/1966
GB        1199683        7/1970
(Continued)

OTHER PUBLICATIONS

Sinnott, R. K., 2.14 Recycle Processes, Chemical Engineering Design, Fourth ed. vol. 6, 2005, 50.*
(Continued)

*Primary Examiner* — In Suk Bullock
*Assistant Examiner* — Jason Chong
(74) *Attorney, Agent, or Firm* — Morrison & Foerster LLP

(57) ABSTRACT

Disclosed is a process for the catalytic dehydrogenation of alkanes so as to form the corresponding olefins. The reaction mixture is subjected to membrane separation of hydrogen, in a separate unit. Preferably a plurality of alternating reaction and separation units is used. The process of the invention serves the purpose of reducing coke formation on the catalyst, and also of achieving a higher alkane conversion without a similar increase in coke formation. The process can also be used for the production of hydrogen.

12 Claims, 3 Drawing Sheets

(52) U.S. Cl.
CPC ........ *C07C 5/3337* (2013.01); *B01D 2256/24* (2013.01); *B01D 2257/108* (2013.01); *C07C 2523/26* (2013.01); *C07C 2523/42* (2013.01); *Y10T 29/49718* (2015.01)

(56) References Cited

U.S. PATENT DOCUMENTS

| | | | | |
|---|---|---|---|---|
| 4,926,005 | A | * | 5/1990 | Olbrich ................ C07C 5/3335 585/632 |
| 5,202,517 | A | | 4/1993 | Minet et al. |
| 5,217,506 | A | * | 6/1993 | Edlund ................ B01D 53/228 55/524 |
| 5,430,218 | A | * | 7/1995 | Miller ................... C07C 5/3337 585/654 |
| 5,439,859 | A | * | 8/1995 | Durante ................ B01J 8/0453 502/168 |
| 5,516,961 | A | * | 5/1996 | Miller .................... B01J 29/068 502/64 |
| 2002/0099248 | A1 | | 7/2002 | Ziaka-Vasileiadou et al. |

FOREIGN PATENT DOCUMENTS

| | | |
|---|---|---|
| GB | 2201159 | 8/1988 |
| WO | WO-95/06018 | 3/1995 |
| WO | WO-2009/158323 | 12/2009 |

OTHER PUBLICATIONS

Armor, "Catalysis with Permselective Inorganic Membranes," Applied Catalysis (1989) 49:1-25.

International Search Report for PCT/NL2012/050201, mailed Jun. 12, 2012, 3 pages.

* cited by examiner

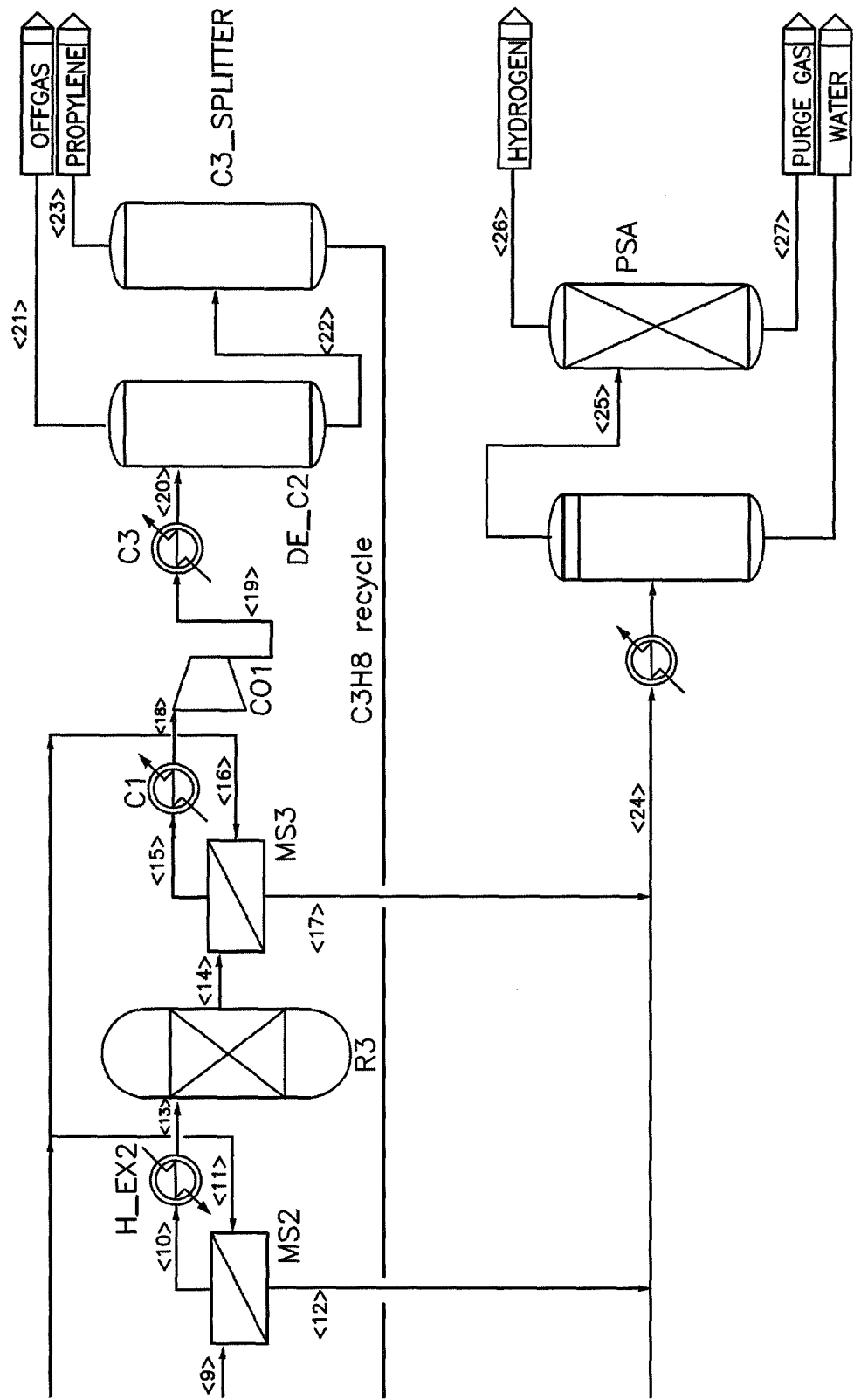
Fig. 2, cont'd

METHOD FOR OLEFINS PRODUCTION

CROSS-REFERENCE TO RELATED APPLICATIONS

This application is the national phase of PCT application PCT/NL2012/050201 having an international filing date of 28 Mar. 2012, which claims benefit of European application No. 11160218.1, filed 29 Mar. 2011. The contents of the above patent applications are incorporated by reference herein in their entirety.

FIELD OF THE INVENTION

The invention is in the field of the production of alkenes (olefins) by the catalytic dehydrogenation of corresponding alkanes. The invention further pertains to a plant for the production of alkenes, and to the use of membrane reactors for the reduction of coke formation in catalytic dehydrogenation of alkanes. The invention particularly concerns producing propene from propane.

BACKGROUND OF THE INVENTION

Olefinic compounds (alkenes) are widely used in a number of chemical industries. To name a few, for the production of petrochemical products, such as synthetic rubbers, plastics, motor fuel blending additives. Among the olefins, propylene (propene) is the world's second largest petrochemical commodity, being the precursor of polypropylene, which is used in such everyday products as packaging materials and outdoor clothing.

Nowadays, light olefins (e.g. ethylene, propylene, isobutene) are commonly obtained by steam cracking (SC) and fluid catalytic cracking (FCC) of light oil fractions. For example, most propylene is produced as co-product in steam crackers (>55%) and as by-product in FCC units (~35%), while only small fraction (<10%) is produced by alternative technologies, such as propane dehydrogenation.

In the case of both SC and FCC, coking and side reactions are among major drawbacks. Another disadvantage of steam cracking is its relatively low selectivity for the desired products. A wide range of products is produced with limited flexibility. This is inherent to the non-catalytic nature of the process.

Catalytic dehydrogenation of alkanes is becoming a growing branch in petrochemical industry as a route to obtain alkenes from low-cost feedstocks of saturated hydrocarbons (alkanes), according to the reaction equation (1):

$$C_nH_{2n+2} \leftrightarrow C_nH_{2n} + H_2 \quad (1)$$

As compared to conventional cracking technologies, catalytic dehydrogenation may provide better selectivity at lower temperatures, lowering also the coke deposition rate.

Specific features of dehydrogenation reactions determine the reaction conditions, process design and the nature of catalysts. Paraffins dehydrogenation reactions are highly endothermic (about 30 kcal/mol for propane) and the yields of target products are limited by thermodynamic equilibrium. According to Le Chatelier's principle, higher conversion will require either higher temperature or lower pressures. In a somewhat abbreviated form for the production of mono-olefins, this can be expressed as follows (2):

$$x_e^2 = \frac{K_p}{K_p + P} \quad (2)$$

wherein $x_e$ is the equilibrium conversion, P the total absolute pressure and $K_p$ is the equilibrium constant for the dehydrogenation reaction.

An equilibrium diagram for the generic reaction (1) at atmospheric pressure is shown in FIG. 1. The temperature necessary to obtain an iso-conversion is dependent on the number of carbon atoms in the molecule: the lower is this value, the higher is the temperature. Temperatures as high as 900° C. and 750° C. are required to achieve a conversion of 90% for ethane and propane at equilibrium, respectively (at atmospheric pressure). To obtain 70% conversion, the corresponding temperatures are 790 and 660° C.

These conditions might be critical for the paraffins and olefins stability: favored by high temperatures, several side reactions take place. E.g., oligomerization to heavier compounds, cracking to lighter hydrocarbons, skeletal isomerization, aromatization, alkylation of the formed aromatic rings, eventually leading to coke formation, and these may lower the yields to olefins. Accordingly, the use of a specific catalyst is necessary in order to keep a suitable conversion while obtaining high selectivity towards the desired olefin. Furthermore, the unavoidable formation of coke on the catalyst surface results in progressive reduction of catalytic activity. Thus, a periodical regeneration of the catalyst is required, generally realized by oxidation of the deposited carbonaceous compounds. In view of the temperatures to be applied in the conversion of propane into propene, the foregoing problem is particularly incurred when producing propene.

Taking two major olefins as illustrative examples, there are two leading processes industrially developed for dehydrogenation of propane to propylene and isobutane to isobutene and they are both operated on a large scale. E.g. the ABB Lummus Catofin process is a cyclic process that uses $Cr_2O_3/Al_2O_3$ catalyst (activated alumina impregnated with 18-20 wt % chromium) in, at least, three fixed bed reactors operating under slight vacuum. With these three reactors, one reactor is processing the alkane feed, one has its catalyst regenerated in situ with air, and the third is purged, so as to give a continuous plant throughput. Fresh and recycle feed are preheated and fed to the reactor at 0.35-0.7 bar pressure. During reaction, coke deposited on the catalyst and combustion of the coke during regeneration re-heats the catalyst bed. During the hydrocarbon processing step, fresh feed and recycle feed from a $C_3$ splitter are vaporized by exchange with various process streams and then raised to reaction temperature in the charge heater. The reactor effluent is cooled, compressed and sent to the purification and separation section.

The UOP Oleflex continuous process uses a $Pt/Sn/Al_2O_3$ catalyst in 3-4 adiabatic (though close to isothermal) moving bed reactors with feed preheat, inter stage heating and continuous catalyst regeneration. The process gets close to thermodynamic equilibrium. Fresh feed is mixed with recycled hydrogen (to reduce coking) and unconverted feed at slightly positive pressure. This process is characterized by high capital outlays because of sophisticated apparatus. Moreover, this technology requires a high mechanical strength of the catalyst.

Typically, to suppress coking during dehydrogenation, hydrogen or water vapor is added to the reaction mixture. The amount of these additives should be optimized. In the case of hydrogen, this is dictated by the fact that it is a reaction product, and, therefore, when added, it shifts the reaction equilibrium to the initial alkane, thereby decreasing the degree of conversion. The introduction of water vapor decreases the selectivity in the target product because of the formation of carbon oxides.

However, it must be taken into account that an additional mechanism of deactivation may occur, due to catalyst particle agglomeration (sintering). This may lead to a reduction in active specific surface area and, as a result, catalyst activity. The resulting deactivated catalytic pellets cannot be regenerated just by combustion of hydrocarbons over the deactivated catalytic bed (like in case of coking); this type of deactivation is rather irreversible. Moreover, periodic regenerations of the catalytic bed (to burn off deposited coke) make the sintering deactivation even more severe.

Updating the existing dehydrogenation methods aimed at increasing the yield of olefin hydrocarbons, process selectivity and reducing the amount of coke deposited on the catalyst is a very important problem today.

One of the various approaches to overcome the limitations of alkanes dehydrogenation is represented by the oxidative dehydrogenation (ODH) of alkanes. With the introduction of an oxidant into the reaction mixture, the reaction becomes exothermic and is able to proceed at much lower temperatures. This in turn reduces the side reactions, such as cracking of alkanes and coke formation. Moreover, the thermodynamic limitations of dehydrogenation can be overcome, since removal of hydrogen from the reactive mixture (by oxidizing $H_2$ to water) shifts the equilibrium toward formation of products (alkenes). Several compounds may be used as oxidizing agents: molecular oxygen, halogens, sulfur compounds; the preferred reactant for industrial purposes is usually considered to be molecular oxygen, because of its low cost and little environmental impact.

U.S. Pat. No. 3,904,703 discloses a method for conducting a dehydrogenation reaction involving the contact of a hydrocarbon feedstock with a sequence of a dehydrogenation catalyst in a first zone, then in a second zone with an oxidation or reducible catalyst and then in a third zone with an adsorbent. The sequence may be repeated as many times as desired depending on the space in the reactor or reactors. However, oxidative dehydrogenation has drawbacks of its own, such as a difficulty of controlling the consecutive oxidation of alkanes/alkenes to carbon oxides, the removal of reaction heat, flammability of the reaction mixture, and the possibility of reaction runaway.

Another approach to overcome the limitations of the dehydrogenation of alkanes is represented by the use of membrane reactors, in which the chemical reaction is coupled with the separation of one of the end products, such as hydrogen. In this manner, it is possible to shift the reaction—in the above equation (1)—to the right side and consequently the conversion rate or final product yield may be enhanced. Significant advantages deriving from the use of membrane reactors are the following: (i) conversion enhancement of equilibrium limited reactions; (ii) achievement of the same performance attained in a traditional reactor at milder operating conditions, such as lower temperature; (iii) reduced capital costs due to the combination of reaction and separation in only one system. Use of Pd or Pd-alloy membranes in catalytic membrane reactors, where the membrane "extracts" hydrogen from a reaction, has been proven experimentally and theoretically to be efficient in enhancing conversions and/or lowering operating temperatures of several types of endothermic, equilibrium-limited reactions of petrochemical industry.

In the scientific and patent literature a great many disclosures deal with hydrocarbon dehydrogenation carried out in the presence of a membrane for hydrogen separation.

GB 1,199,683 discloses a process for catalytic dehydrogenation, dehydrocyclization or hydrodealkylation of hydrocarbons having from 2 to 20 carbon atoms, in which the same catalyst acts as membrane for hydrogen separation being based on metals permselective to hydrogen. In one example, a constant catalyst activity for 200 hours was disclosed.

U.S. Pat. No. 5,202,517 discloses a process for dehydrogenation of an alkane or a mixture of alkanes using a tubular ceramic membrane impregnated with a catalytically active metallic substance and a pelletized catalyst material adjacent to the side of the membrane. In the specific case of ethane dehydrogenation to ethylene, conversion levels equivalent to two to five times normal thermodynamic equilibrium in the combined exit gas at temperatures of 500 to 600° C. were obtained.

GB 2 201 159 discloses a process and apparatus for the dehydrogenation of organic compounds using a ceramic membrane permselective to hydrogen. The use of a ceramic membrane is justified as a heat supplier for a dehydrogenation reactor when conducted through by an electric current. In one example, an about 46% increase in propane conversion is observed.

U.S. Pat. No. 5,430,218 discloses a catalytic paraffins dehydrogenation process characterized by hydrocarbon improvement conversion under the hydrogen removal by a thermally stable polymer-porous solid membrane. An increase in feedstock conversion is observed in the presence of the membrane, which furthermore does not adversely affect the overall selectivity.

US 2002/0099248 A1 discloses an integrated process for olefin and polyolefin production via polymerization steps. The process utilizes membrane type permeators downstream of the polymerization reactor for separation of the unconverted olefins from paraffins. In one embodiment the produced propylene obtained after the hydrogen removal is employed for the production of acrolein and acrylic acid.

GB 1,039,381 refers to the use of a membrane reactor in a variety of process that produce hydrogen. As an example, hydrocarbon dehydrogenation reactions are mentioned. It is referred to, inter alia, that lower temperatures can be realized, which would allow the use of a wider choice of catalysts. The process is conducted using a single unit, viz. a compartmented reactor, containing a reaction chamber and a diffusion chamber, or containing a plurality of reaction zones.

U.S. Pat. No. 5,430,218 refers to the use of polymeric membranes for hydrogen separation. As a result, a decoupling of the dehydrogenation reaction processes and membrane separation processes is required. This is presented as an advantage, in view of the necessary regeneration of the dehydrogenation catalyst as a result of coke formation. Hence, the reference essentially accepts the phenomen of coke formation as is, and does not teach the skilled person how to reduce coke formation.

Despite all that is known in the area of membrane reactors, including its use in catalytic dehydrogenation of alkanes, the main lack in the traditional technology is still the higher amount of coke deposited on the catalyst. Reducing this amount would provide for the realization of a continuous process avoiding the necessity of catalyst regeneration.

Furthermore, it is desired to provide processes for the catalytic dehydrogenation of alkanes that allow a higher alkane conversion, yet without a similar promotion of coke formation. Also, it would be desired to provide a method to modernize existing olefin production plants in terms of lower coke formation and/or higher conversion rates.

It is particularly desired to provide a process that allows the foregoing drawbacks to be obviated specifically in the production of propene from propane.

SUMMARY OF THE INVENTION

In order to better address one or more of the foregoing desires, the invention presents, in one aspect, a method for the production of an alkene by the dehydrogenation of a corresponding alkane, comprising the steps of:
(i) providing a hydrocarbon source comprising at least one alkane;
(ii) subjecting the hydrocarbon source to a dehydrogenation reaction in the presence of a dehydrogenation catalyst, so as to form a reaction mixture comprising the alkene corresponding to the alkane, and hydrogen;
(iii) subjecting the reaction mixture to membrane separation, so as to form a permeate comprising hydrogen and a retentate comprising alkene;
(iv) purifying alkene from the retentate;
(v) recycling unconverted alkane;
wherein the dehydrogenation reaction and the membrane separation are conducted in separate units.

The invention, in another aspect, pertains to the use of a membrane separation unit in connection with a catalytic dehydrogenation reactor for the production of an alkene by the dehydrogenation of a corresponding alkane, for the purpose of reducing the formation of carbonaceous substances associated with said production of the alkene.

In a still further aspect, the invention pertains to a plant for the production of an alkene by the dehydrogenation of a corresponding alkane, said plant comprising a series of at least two reaction units alternating with at least two membrane separation units, the membrane separation units being positioned downstream of the reaction units.

In yet another aspect, the invention pertains to a method of modernizing an existing olefin production plant comprising a plurality of hydrogenation reactors, by placing membrane separation modules between the existing reactors.

DETAILED DESCRIPTION OF THE INVENTION

Figure 1:
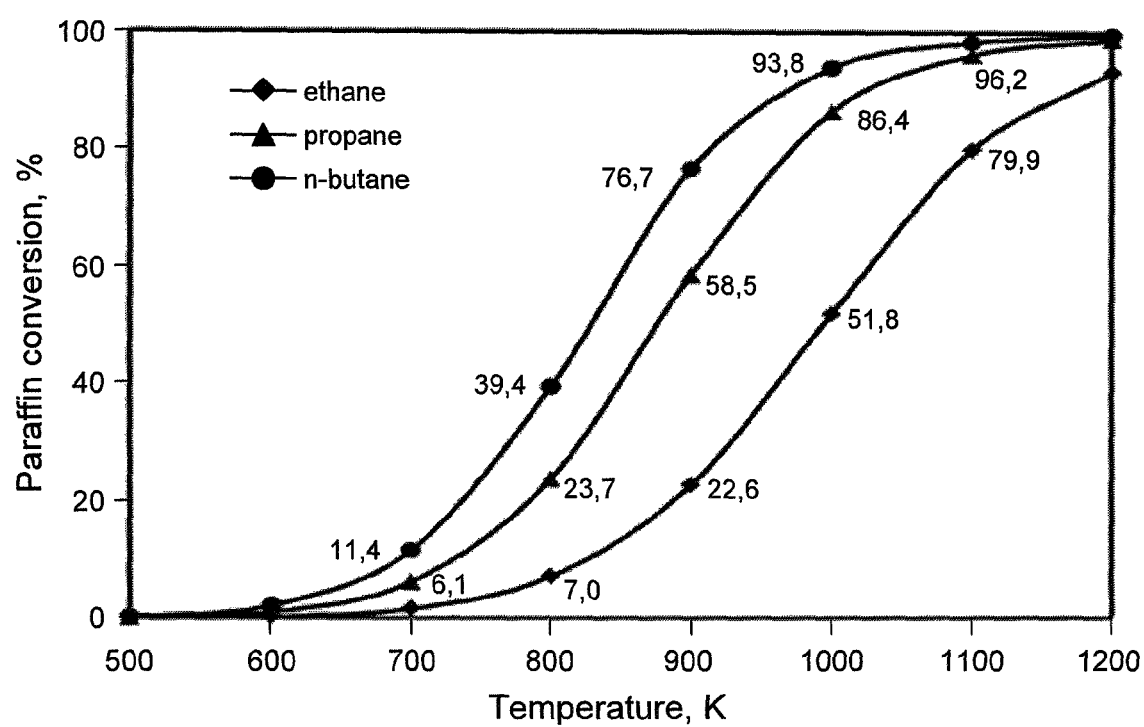
FIG. 1 is a graph showing equilibrium conversion of $C_2$-$C_4$ paraffins to their olefins.

In a broad sense, the invention is based on the judicious recognition that the application of membrane separation units, is capable of minimizing the amount of coke (carbonaceous substances) deposited on the catalytic bed during the production of olefins by alkane dehydrogenation, and particularly while reaching the same alkane conversion at lower temperature with both a higher selectivity and overall system efficiency. Although not wishing to be bound by theory, the inventors believe that the withdrawal of the produced hydrogen from the reaction product mixture, by a plurality of membrane separation modules, is capable of reducing the extent of cracking reactions.

According to the invention, the dehydrogenation reaction and the hydrogen separation are carried out in separate units. I.e., the reactor (reaction unit) and the membrane separation module (separation unit) are such separate entities as to allow the process conditions (pressure, temperature) to be controlled independently in either unit. Typically, said reaction and separation units are not integrated into a single confinement.

As a result of this "open architecture", the dehydrogenation reactor and the separation module can be performed independently and each step can operate at its own optimized conditions. Typically in order to avoid membranes' stability problems, the temperature in a membrane separation module is maintained slightly below 500° C. and preferably in the range of 420-490° C., more preferably at 450-470° C. An advantage of the "open architecture" is that it allows the temperature for the separation step to be optimized independently. As a result, a problem incurred in the art, viz. a reported embrittlement of metal membranes, particularly palladium membranes, can be avoided.

In the traditional membrane reactors applied to a dehydrogenation reactor, the membrane is integrated inside the reaction chamber thus providing for a continuous removal of hydrogen as soon as it is produced. Whilst the reduction of hydrogen partial pressure might enhance the alkane conversion, it may also promote the carbon formation. The invention judiciously avoids this. Since the produced hydrogen is removed outside of the reaction chamber, the hydrogen partial pressure in the reactor increases with the reaction's progress. A further advantage is that the use of separate modules limits the mechanical problems relevant to the integration of the membrane inside the catalytic bed and enables for the rearrangement of already existing plants.

Preferably, the dehydrogenation process is performed in an open architecture based plant in several steps, or stages, in the sense that the reaction takes place in one or more reactors and the separation of hydrogen from the alkene rich mixture in one or more membrane separation modules. By involving several dehydrogenation steps, a higher alkane conversion into the corresponding olefin can be achieved, which is advantageous especially in combination with a lower operating temperature than the industrial employed one. Preferably, two, three or four stages are used, and most preferably, three.

Thus, the above steps (i) to (iii) are preferably repeated one or more times in subsequent dehydrogenation reaction units and membrane separation units. In doing so, unreacted alkane in the retentate from a preceding membrane separation step is used as the hydrocarbon source in a subsequent dehydrogenation step. It will be understood that purifying the alkene from the retentate can, in theory, be done after each membrane separation step, but will preferably be done only after the last step in a series of reaction and separation steps. Hence, the repeated reactions will be done on the basis of mixtures comprising alkene formed in a previous dehydrogenation step, and unreacted alkane from such a step, and thus furthering the conversion from alkane to alkene with each subsequent dehydrogenation reaction step. After the last membrane separation step in a series of reaction and separation steps, the unconverted alkane (with the alkene removed) will be recycled and be used as the alkane source in the first dehydrogenation step of said series, i.e. in a new dehydrogenation cycle. Said new dehydrogenation cycle itself will again comprise the aforementioned series of dehydrogenation and separation steps, wherein the conversion to alkene is furthered, and wherein after the last separation step the unconverted alkane is again isolated from the alkene, and recycled to yet a further dehydrogenation cycle.

The method of the invention can be performed on a wide variety of hydrocarbon sources comprising one or more alkanes. This generally refers to any fossil fuel rich mixture. Under fossil fuel it is understood here carbon containing natural fuel material and preferably gas material such as natural gas, methane, ethane, propane, butane and mixtures thereof. Preferably, light hydrocarbons (preferably $C_2$-$C_4$) are used in the dehydrogenation reaction according to the invention. In the present invention preferably propane or ethane is used. Nevertheless, in general, the invention is applicable on all alkanes that can be subject to catalytic dehydrogenation. This wide choice of alkanes is known to the skilled person. Suitable alkanes, e.g., are straight-chain or branched alkanes having chain lengths of 2 to 20 carbon atoms. Preferably, the invention is employed on $C_2$-$C_{10}$ alkanes, and more preferably on $C_2$-$C_6$ alkanes. Most preferably, the invention is used in the production of light olefins ($C_2$-$C_4$), such as ethylene, propylene, or iso-butene, starting from the corresponding ($C_2$-$C_4$) alkanes.

It should be noted that the problems associated with side-reactions, and particularly with coke formation, are clearly more pronounced in the case of propane than in the case of butane. Reference is made to FIG. 1, which shows the conversion of ethane, propane and n-butane as a function of the temperature. With respect to propane and n-butane, within the critical temperature range of 700-850K, the temperature difference to reach the same conversion, for propane is about 50° C. higher than for n-butane. Thus, propane behaves clearly less favourably than n-butane.

In all instances, the process can be operated on starting materials that either provide a mixture of alkanes, or a specific isolated alkane. The starting materials can be purified or crude.

Suitable dehydrogenation catalysts, and methods of conducting the catalytic dehydrogenation reaction, are known in the art. Thus the process conditions for catalytic dehydrogenation are well known to a person skilled in the art. Reference is made, e.g., to "Chemical Process Technology" by J. A. Moulijn, M. Makkee, A. van Diepen (2001) Wiley.

Generally, before entering the dehydrogenation environment, an alkane rich mixture is compressed (e.g. in the case of a propane-rich gas mixture) up to 5-10 barg and pre-heated, e.g. in a charge heater, to the reaction temperature, and directed to the dehydrogenation reactor at an atmospheric or sub-atmospheric pressure. Generally, the catalytic dehydrogenation reaction takes place at temperatures ranging between 550-700° C. and at sub-atmospheric pressure, preferably 0.5-0.7 atm or slightly above. Typical dehydrogenation catalysts contain platinum or chromium. In a preferred embodiment Cr based catalysts deposited on $Al_2O_3$ are used.

In the state of the art, the alkane (e.g. propane) frequently is fed at atmospheric or sub-atmospheric pressure. In the process of the invention it is preferred to feed compressed alkane, since the membrane separation is favoured by high partial pressure difference between retentate and permeate side.

After the dehydrogenation reaction, the resulting reaction mixture (e.g. a gas mixture comprising propylene and hydrogen) is carried to a membrane separator, typically based on palladium or palladium alloy, to separate the hydrogen. According to the invention, the hydrogen separation takes place in a membrane separation module which is provided as a separate unit from the dehydrogenation reactor.

Membranes for separation of hydrogen are known. Generally, these can be polymeric membranes or metal membranes. Metal membranes are preferred, with palladium or palladium alloys such as for example Pd—Ag being the most preferred.

In connection with polymeric membranes, reference is made to the above-mentioned U.S. Pat. No. 5,430,218. As mentioned earlier, the process disclosed therein does not address the reduction of coke formation. Rather, it suggests the use of membrane separation in view of the necessary catalyst regeneration. In fact, the reference is limited in its teaching to the step of hydrogen separation, it does not disclose an economically and industrially feasible process scheme, and thus does not teach that in such a process the use of membrane separation, in a unit separate from the reaction unit, allows achieving a reduction of coke formation. The invention, on the other hand, is based on the recognition that coke formation is reduced in a method as described above, including the steps of, after a dehydrogenation cycle, purifying the alkene from the retentate, and recycling unconverted alkane so as to make it available for another dehydrogenation cycle.

In the invention, it is preferred to employ metallic rather than polymeric membranes. This is of advantage, since the higher stability of metallic membranes, as compared to polymeric membranes, allows the hydrogen separation to be conducted at a temperature of the same order of magnitude, and preferably just the same temperature, as the temperature at the reactor outlet. The use of polymeric membranes would require cooling to a temperature below 300° C. Particularly in the preferred embodiment wherein a plurality of reactor/separator units are employed in line, it is advantageous to avoid cooling, since the next reactor unit will desirably operate at a reaction temperature of the original order of magnitude. Hence, the lower the temperature at the separation units, the higher the temperature difference that needs to be overcome until the desired reaction temperature is reached.

It is noted that if the preference is realized of having a plurality of reactors, placed in series, operate at about the same reaction temperature, a heating step is included between the hydrogen separation unit and the next reactor unit. Other than in the case of using a polymeric membrane, this is merely because the dehydrogenation reaction is endothermic, i.e. the temperature at the reactor outlet will be lower than at the onset of the reaction. Thus, in a preferred embodiment, the invention is a process as described above, wherein the alkane to be dehydrogenated is pre-heated prior to entry into a next dehydrogenation reactor.

Thus, in one embodiment, the invention provides a method for the production of an alkene by the dehydrogenation of a corresponding alkane, comprising the steps of:
(i) providing a hydrocarbon source comprising at least one alkane;
(ii) subjecting the hydrocarbon source, at a temperature of 450°-650° C., preferably 500°-550° C., to a dehydrogenation reaction in the presence of a dehydrogenation catalyst, so as to form a first reaction mixture comprising the alkene corresponding to the alkane, and hydrogen;
(iii) subjecting the reaction mixture to membrane separation, so as to form a permeate comprising hydrogen and a first retentate comprising alkene and unreacted alkane;

(iv) heating the first retentate to a temperature of 500° C.-550° C.;
(v) feeding the first retentate to a dehydrogenation reactor so as to subject the unreacted alkane to a dehydrogenation reaction in the presence of a dehydrogenation catalyst, so as to form a second reaction mixture comprising the alkene corresponding to the alkane, and hydrogen;
(vi) subjecting the second reaction mixture to membrane separation, so as to form a permeate comprising hydrogen and a second retentate comprising alkene and unreacted alkane;
(vii) optionally repeating steps (iv) to (vi) one or more times with the second retentate and one or more subsequent retentate formed from said repetition of steps;
(viii) purifying the alkene from the last retentate;
(ix) recycling unconverted alkane so as to make it available for the dehydrogenation reaction;
wherein the dehydrogenation reactions and the membrane separations are conducted in separate units.

Preferably, the dehydrogenation process is performed in an open architecture based plant in several steps, or stages, in the sense that the reaction takes place in one or more reactors and the separation of hydrogen from the alkene (e.g. propylene) rich mixture in one or more membrane separation modules. By involving several dehydrogenation steps, a higher alkane conversion into the corresponding olefin can be achieved, which is advantageous especially in combination with a lower operating temperature than the industrial employed one. Preferably, two, three or four stages are used, and most preferably, three. Thus, in a preferred embodiment the invention provides a method as described above, comprising a plurality of dehydrogenation steps and a plurality of membrane separation steps, wherein a first dehydrogenation step followed by a first membrane separation step, and said dehydrogenation steps and said membrane separation steps are alternating. More preferably, said method comprises 3-4 dehydrogenation steps and 3-4 membrane separation steps.

The retentate of the membrane separation module containing alkene and unreacted hydrocarbons and dehydrogenation reaction by-products is fed either to the inlet of the following dehydrogenation step (when several dehydrogenation step are employed) or, in the case of the last membrane separation module is fed to a purification section. Said purification section comprising one or more units in which products, by-products, and unreacted starting materials can be separated. E.g., a separation unit of $C_2$ based by-products from alkene containing mixture and a separation unit of propylene from unreacted propane. Preferably, the residual of the first separation unit is carried to the aforementioned charge heater as a fuel, meanwhile the unreacted propane is recycled and mixed with fresh alkane.

The permeate of the membrane separation module contains mainly hydrogen and sweeping steam (i.e. water vapour). The hydrogen can easily be separated from the steam by condensation of the steam. Preferably, separated hydrogen is further compressed and purified by pressure swing adsorption (PSA). If $CO_2$ is used as sweeping gas, the permeate mixture can be directly routed to methanol synthesis. Other uses include, e.g., ammonia synthesis, oil refining, electronics, steel industry.

Figure 2:
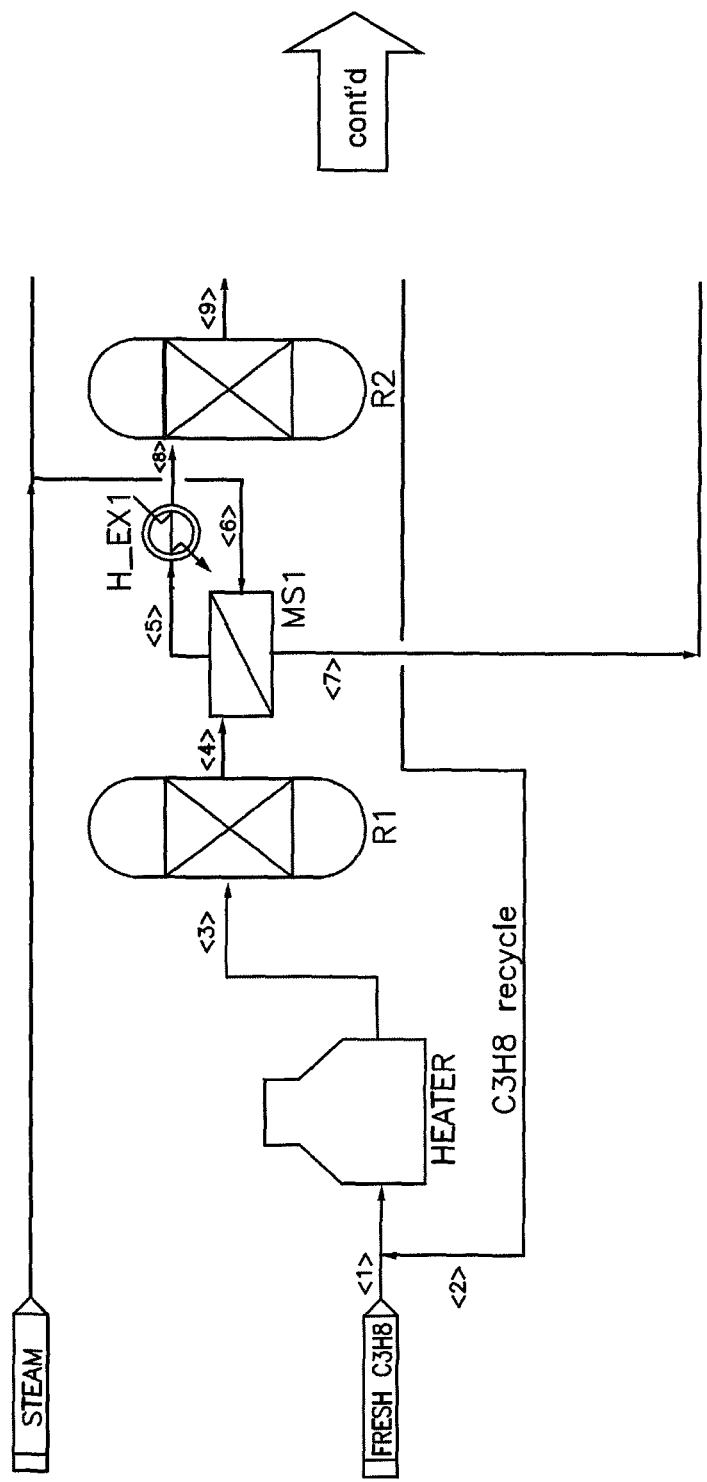
FIG. 2 shows a process scheme for a preferred embodiment of the invention wherein three dehydrogenation reactors are coupled to three membrane separation modules. Details including pumps, compressors, instrumentation and control loop and other items not essential to the understanding of the invention are not shown.

In FIG. 2 a process scheme for a preferred embodiment is shown, wherein the dehydrogenation reaction is carried out in three steps and the permeate of the separation module is sent to a Pressure Swing Adsorption unit.

In this scheme, fresh propane (1) is mixed with unconverted recycled propane, compressed and preheated in a charge heater up to 450-550° C. before being fed (3) to the first dehydrogenation reactor R1, where the catalytic dehydrogenation reaction takes place. The exhaust stream (4) coming from the first reactor is at a temperature suitable to be fed to the first separation module MS1. Sweeping steam (6) is sent to the permeate side of the membrane to reduce the hydrogen partial pressure with a consequent improvement of hydrogen permeation.

The permeate stream (7) comprising hydrogen and sweeping steam is mixed with the other permeate streams (12) and (17) and sent (24) to a cooler for steam condensation and finally (25) to a Pressure Swing Adsorption unit for further hydrogen recovery (26) also yielding purge gas stream (27).

The retentate (5) from the first membrane module is preheated to the reaction temperature (H_EX1) and further sent (8) to the second dehydrogenation reactor R2. The produced mixture comprising propylene and hydrogen (9) is routed to the second membrane separation module MS2. The retentate stream (10) is further sent to a preheating section (H_EX2) and enters (13) the third dehydrogenation reactor R3.

The produced mixture comprising propylene and hydrogen (14) is routed to the third membrane separation module MS3. The retentate stream (15) is cooled (C1) and the resulting stream (18) is compressed (CO1) giving a stream (19). Stream (19) is subjected to another cooling step (C3) and the resulting stream (20) is sent to a deethanizer column (DE_C 2) which produces a lighter fraction or offgas (21) rich in ethane and a heavier fraction (22) comprising propylene and unreacted propane. This stream is sent to a further separation column, C3_SPLITTER, from which a propylene stream (23) and a propane stream (2) are obtained. The propane stream (2) is recycled and mixed with fresh propane.

In this process scheme the ethane rich mixture or offgas from deethanizer and the purge gas from Pressure swing adsorption unit can provide all or part of reaction heat to the three dehydrogenation reactor, as well as the heat necessary to produce the sweeping steam.

The scheme presented in FIG. 2 is able to work at temperature in the range 450-550° C. which are lower than that of conventional technologies, however realizing the same feed conversion but a higher selectivity estimated in 5-10% more, with sensible reduction of coke amount deposited on the catalyst which will not require the continuous regeneration. From the energy point of view, the use of an open architecture based membrane reactor with 2-4 stages of membrane separation allows to produce propylene with a higher overall efficiency.

The invention also relates to the use of a membrane separation unit in connection with a catalytic dehydrogenation reactor for the production of an alkene by the dehydrogenation of a corresponding alkane, for the purpose of reducing the formation of coke associated with said production of the alkene. This is a specific purpose, leading to considerable advantage in catalytic dehydrogenation, that is not foreseen in existing uses of membrane separators. In a still further aspect, the invention pertains to a plant for the production of an alkene by the dehydrogenation of a corresponding alkane, said plant comprising a series of at least two reaction units alternating with at least two membrane separation units, the membrane separation units being positioned downstream of the reaction units, and wherein the reaction units and the membrane separation units are such separate entities as to allow the process conditions (pressure, temperature) to be controlled independently in all units. The plant, in deviation from existing plants, is thus characterized by the "open architecture" mentioned above. As a result thereof, the dehydrogenation reactor and the separation module can be performed independently and each step can operate at its own optimized conditions.

The aforementioned "open architecture" also contributes to an advantageously straightforward, and relatively simple, method by which the invention allows providing a method of modernizing an existing olefin production plant comprising a plurality of hydrogenation reactors. Accordingly, said method comprises placing membrane separation modules between the existing reactors. Thus, the existing plant can be modernized and be converted into a plant that is less prone to the side-effects of coking, by the relatively simple addition of units that perform the function of membrane separation. Since such membrane separation units themselves are familiar in the art, the skilled person will have no substantial difficulties in placing these units at the right positions, and making the right connections between the newly placed units and the existing ones. It will be understood, that the infrastructure of the plant, e.g. energy supply lines, gas flow lines, control systems, will normally require to be upgraded in order to accommodate the operation of the additional units. This is well within the ambit of the skilled persons regular skills.

The invention claimed is:

1. A method for producing an alkene by dehydrogenation of a corresponding alkane to the alkene, comprising the steps of:
   (i) providing a hydrocarbon source comprising at least one alkane;
   (ii) dehydrogenating the hydrocarbon source in the presence of a dehydrogenation catalyst to form a reaction mixture comprising hydrogen and an alkene corresponding to the at least one alkane
   (iii) separating the reaction mixture in a metal membrane to form a permeate comprising hydrogen and a retentate comprising unconverted alkane and the alkene corresponding to the at least one alkane;
   (iv) purifying the alkene from the retentate comprising the alkene and the unconverted alkane;
   (v) recycling the unconverted alkane in (iv);
   wherein the dehydrogenation reaction and the membrane separation are conducted in separate units,
   wherein the dehydrogenation in (ii) is conducted at a temperature of 500-650° C. and the separation in (iii) is conducted at a lower temperature of 420-490° C., and
   wherein said method comprises a plurality of dehydrogenation steps (ii) and a plurality of separation steps (iii), wherein each dehydrogenation step is followed by a separation step, and wherein the retentate from each separation step is subjected to a subsequent dehydrogenation step such that said dehydrogenation steps and said separation steps are alternating.

2. The method according to claim 1, wherein the recycled unconverted alkane is pre-heated to 500-650° C. prior to conducting the subsequent dehydrogenation step.

3. The method according to claim 1, comprising 3 or 4 dehydrogenation steps and 3 or 4 membrane separation steps.

4. The method according to claim 1, wherein the alkane to be dehydrogenated is selected from the group consisting of ethane, propane, butane and mixtures thereof.

5. The method according to claim 1, wherein the separation in (iii) and (vi) comprises providing a permeate side of the membrane with a sweeping steam so as to reduce a partial pressure of hydrogen.

6. The method of claim 1, which further comprises separating the hydrogen from the permeate.

7. The method according to claim 6, wherein the separation in (iii) comprises sending a sweeping steam to a permeate side of the metal membrane to reduce a partial pressure of hydrogen and produce a permeate comprising hydrogen and steam, and separating the hydrogen by allowing the steam to condence.

8. The method of claim 1 wherein the membrane comprises palladium.

9. A method for producing an alkene by dehydrogenation of a corresponding alkane to the alkene, comprising the steps of:
   (i) providing a hydrocarbon source comprising at least one alkane;
   (ii) dehydrogenating the hydrocarbon source at a temperature of 500-650° C. in the presence of a dehydrogenation catalyst in a first dehydrogenation reactor to form a first reaction mixture comprising hydrogen and an alkene corresponding to the at least one alkane;
   (iii) separating the first reaction mixture in a first metal membrane, located in a separate unit from the first dehydrogenation reactor, at a temperature of 420-490° C. to form a first permeate comprising hydrogen and a first retentate comprising unconverted alkane and the alkene corresponding to the at least one alkane;
   (iv) heating the first retentate to a temperature of 500° C.-550° C.;
   (v) dehydrogenating the first retentate in a second dehydrogenation reactor in the presence of the dehydrogenation catalyst to form a second reaction mixture comprising hydrogen and the alkene corresponding to the at least one alkane;
   (vi) separating the second reaction mixture in a second metal membrane, located in a separate unit from the second dehydrogenation reactor, to form a second permeate comprising hydrogen and a second retentate comprising unconverted alkane and the alkene corresponding to the at least one alkane;
   (vii) optionally repeating steps (iv) to (vi) one or more times with the second retentate and one or more subsequent retentate formed from said repetition of steps;
   (viii) purifying the alkene from a last retentate comprising the alkene and the unconverted alkane;
   (ix) recycling the unconverted alkane in (viii).

10. The method according to claim 9, wherein the alkane to be dehydrogenated is selected from the group consisting of ethane, propane, butane and mixtures thereof.

11. The method according to claim 9, wherein the separation in (iii) and (vi) comprises sending a sweeping steam to a permeate side of the metal membrane to reduce a partial pressure of hydrogen.

12. The method of claim 9 wherein the temperature in (ii) is 500-550° C.

* * * * *